United States Patent
Baas et al.

(10) Patent No.: US 9,974,532 B2
(45) Date of Patent: May 22, 2018

(54) CLIP FOR ORGAN RETRACTION DURING MINIMALLY INVASIVE SURGERY

(71) Applicants: Surgical Perspective SAS, Strasbourg (FR); IRCAD, Strasbourg (FR)

(72) Inventors: David Baas, Strasbourg (FR); Vincent Garitey, Marseilles (FR); Frederic Mouret, Marseilles (FR); Bernard Dallemagne, Beaufays (BE); Silvana Perretta, Strasbourg (FR)

(73) Assignees: SURGICAL PERSPECTIVE SAS, Strasbourg (FR); IRCAD, Strasbourg (FR)

( * ) Notice: Subject to any disclaimer, the term of this patent is extended or adjusted under 35 U.S.C. 154(b) by 389 days.

(21) Appl. No.: 14/346,703

(22) PCT Filed: Sep. 21, 2012

(86) PCT No.: PCT/IB2012/002130
§ 371 (c)(1),
(2) Date: Mar. 21, 2014

(87) PCT Pub. No.: WO2013/041960
PCT Pub. Date: Mar. 28, 2013

(65) Prior Publication Data
US 2014/0235936 A1    Aug. 21, 2014

Related U.S. Application Data

(60) Provisional application No. 61/538,677, filed on Sep. 23, 2011.

(51) Int. Cl.
*A61B 17/02* (2006.01)
*A61B 17/08* (2006.01)

(52) U.S. Cl.
CPC ........ *A61B 17/0218* (2013.01); *A61B 17/083* (2013.01); *A61B 2017/0225* (2013.01)

(58) Field of Classification Search
CPC . A61B 17/02; A61B 17/0218; A61B 17/0293; A61B 17/08; A61B 17/083;
(Continued)

(56) References Cited

U.S. PATENT DOCUMENTS 6,251,117 B1 * 6/2001 Kringel .............. A61B 17/1227
606/158
7,112,172 B2 * 9/2006 Orban, III .......... A61B 17/0218
600/204

(Continued)

FOREIGN PATENT DOCUMENTS

DE    10 2009 01429    12/2010
EP    2283778    2/2011
(Continued)

OTHER PUBLICATIONS

PCT/IB2012/002130 International Search Report and Written Opinion dated Jan. 21, 2013.
(Continued)

*Primary Examiner* — Ryan J Severson
(74) *Attorney, Agent, or Firm* — Wilson Sonsini Goodrich & Rosati

(57) ABSTRACT

Provided herein is a clip for organ retraction or organ exposure during minimal invasive surgery wherein the clip comprises a body made of a biocompatible material wherein the body comprises at least two generally opposing first and second segments that form a jaw defined by a separation between the two segments; wherein the two segments each comprise distal and proximal ends wherein the proximal ends may be directly connected or connected through one or more segments within the body of the clip and wherein the
(Continued)

open configuration clip defines at least four configurations a resting configuration, an open configuration, a grabbing configuration, and a sliding configuration.

31 Claims, 18 Drawing Sheets

(58) Field of Classification Search
CPC ..... A61B 17/10; A61B 17/105; A61B 17/122; A61B 17/1222; A61B 17/1227; A61B 17/128; A61B 17/1285; A61B 2017/0225; A61B 2017/0287; A61B 2017/081
See application file for complete search history.

(56) References Cited

U.S. PATENT DOCUMENTS

| | | | |
|---|---|---|---|
| 7,520,884 B2 * | 4/2009 | Swanstrom | A61B 17/00234 606/153 |
| 8,075,481 B2 * | 12/2011 | Park | A61B 17/0218 600/204 |
| 8,133,255 B2 * | 3/2012 | Ravikumar | A61B 90/50 606/167 |
| 8,251,889 B2 * | 8/2012 | Scott | A61B 17/0218 600/204 |
| 8,852,088 B2 * | 10/2014 | Ransden | A61B 17/0401 600/204 |
| 8,888,679 B2 * | 11/2014 | Scott | A61B 17/0218 600/37 |
| 9,107,648 B2 * | 8/2015 | Ransden | A61B 17/0401 |
| 9,241,698 B2 * | 1/2016 | Ransden | A61B 17/0401 |
| 9,247,932 B2 * | 2/2016 | Lee | A61B 17/0218 |
| 9,326,784 B2 * | 5/2016 | Ravikumar | A61B 90/50 |
| 9,549,727 B2 * | 1/2017 | Scott | A61B 17/0218 |
| 2004/0254427 A1 * | 12/2004 | Fowler, Jr. | A61B 17/02 600/210 |
| 2005/0203344 A1 * | 9/2005 | Orban, III | A61B 17/0218 600/204 |
| 2005/0250980 A1 * | 11/2005 | Swanstrom | A61B 17/00234 600/37 |
| 2007/0213767 A1 * | 9/2007 | Ravikumar | A61B 17/221 606/205 |
| 2007/0250112 A1 * | 10/2007 | Ravikumar | A61B 17/221 606/205 |
| 2010/0174150 A1 * | 7/2010 | Park | A61B 17/0218 600/218 |
| 2012/0078057 A1 * | 3/2012 | Scott | A61B 17/0218 600/201 |
| 2013/0190572 A1 * | 7/2013 | Lee | A61B 17/0218 600/204 |
| 2013/0253275 A1 * | 9/2013 | Ransden | A61B 17/0218 600/204 |
| 2014/0114332 A1 * | 4/2014 | Lutze | A61B 17/083 606/151 |

FOREIGN PATENT DOCUMENTS

| | | |
|---|---|---|
| GB | 13512 | 4/1906 |
| WO | WO 2003-096907 | 11/2003 |
| WO | WO 2010-042884 | 4/2010 |
| WO | WO 2010-099327 | 9/2010 |
| WO | WO 2013-041960 | 3/2013 |

OTHER PUBLICATIONS

PCT/IB2012/002130 International Report on Patentability dated Apr. 3, 2014.

* cited by examiner

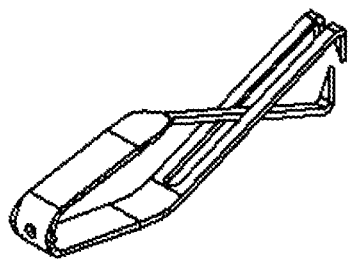
FIG 2-a : sliding configuration
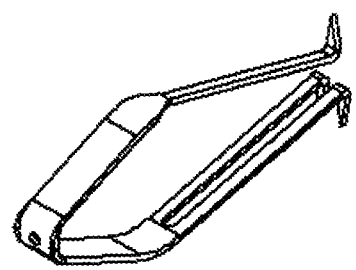
FIG 2-c: resting configuration
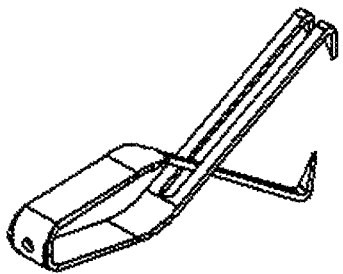
FIG 2-b : open configuration
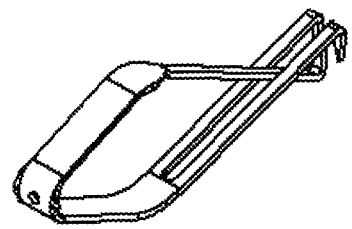
FIG 2-d : grabbing configuration Figure 12 Element for adjusting the distance between the two clips.

Figures 15 (a, b, c)

CLIP FOR ORGAN RETRACTION DURING MINIMALLY INVASIVE SURGERY

RELATED APPLICATIONS

This application is a U.S. National Phase application of PCT/IB2012/002130, filed Sep. 21, 2012; which claims the benefit of priority of U.S. Application Ser. No. 61/538,677, filed Sep. 23, 2011; both of which are incorporated herein by reference in their entirety.

BACKGROUND

Minimally invasive (laparoscopic) surgery refers to a type of operation performed through small abdominal incisions in order to reduce traumatic complications and risks associated with conventional surgery. Surgical field exposure still remains a significant challenge for standard laparoscopic techniques and is important for the advancement of Single Incision Laparoscopic Surgery (SILS) and Natural Orifice Transluminal Endoscopic Surgery. Surgical risks related to poor and insufficient field exposure such as lack of visibility, limited space, poor comfort level, adjacent tissue perforation and poor control of surgical field space are still predominant in minimally invasive techniques. Surgeons are compensating for the lack of dedicated instruments by using indirect approaches and tricks to increase field space. Steep reclining position (Trendelenburg position) and high $CO_2$ levels are commonly used in surgery to augment field space. These techniques have been associated with significant peri- and post-operative complications, particularly with fragile patients and obese people. Field exposure is even more difficult to achieve in SILS procedures and impacts surgical outcome significantly. The lack of dedicated retraction instruments for SILS remains a barrier to its use and expansion.

Single use surgical retractors are instruments used to easily hold back tissues and expose underlying body parts.

Thus there is a need for a system and method for organ retraction during minimally invasive surgery. The disclosure presented herein meets this need and provides related advantages as well. There remains a need for powerful retraction means that simplify operating field access and provide increased visibility by optimizing exposure and improving control.

SUMMARY

Provided herein is a clip for organ retraction or organ exposure during minimal invasive surgery wherein the clip comprises a body made of a biocompatible material wherein the body comprises at least two generally opposing first and second segments that form a jaw defined by a separation between the two segments; wherein the two segments each comprise distal and proximal ends wherein the proximal ends may be directly connected or connected through one or more segments within the body of the clip and wherein the clip defines at least four configurations a resting configuration, an open configuration, a grabbing configuration, and a sliding configuration.

Another embodiment provides a clip wherein the resting configuration, the open configuration, the grabbing configuration, and the sliding configuration are as illustrated in FIGS. 2 A-D.

Another embodiment provides a clip wherein the biocompatible material has an elasticity that allows changing the configuration of the clip while the clip is deployed in a cavity of a patient's body.

Another embodiment provides a clip wherein the biocompatible comprises an elastomeric material and/or metallic material.

Another embodiment provides a clip wherein changing the configuration of the clip is carried out using an ancillary.

Another embodiment provides a clip wherein the ancillary allows in a single movement to change the configuration of the clip from the sliding configuration to the open configuration and then to the grabbing configuration.

Another embodiment provides a clip wherein the ancillary allows in a single movement to change the configuration of the clip from the sliding configuration to the open configuration and then to the resting.

Another embodiment provides a clip wherein the ancillary allows in a single movement to change the configuration of the clip to pass from the resting configuration to the open configuration and then to the sliding configuration.

Another embodiment provides a clip wherein the ancillary allows in a single movement to change the configuration of the clip from the grabbing configuration to the open configuration and then to the sliding configuration Another embodiment provides a clip wherein the clip is sized so it can be introduced into a mammal body cavity through a trocar having an opening having a maximum dimension of 12 mm or less Another embodiment provides a clip wherein the clip is adapted for introduction and grabbing of an organ within five minutes or less.

Another embodiment provides a clip wherein the clip is capable of moving an organ or tissue having a weight of up to 2 kg.

Another embodiment provides a clip wherein the clip is capable of moving an organ or tissue having a weight of at least 1.5 kg.

Another embodiment provides a clip wherein the distal end of the first segment comprises a single branch and the distal end of the second segment comprises two branches that form a U-shape wherein in a closed configuration of the clip the branch of the first segment fits in the U-shape formed by the two branches of the second segments thereby allowing the two segments to cross.

Another embodiment provides a clip having a gripping strength adjustable by selection of the biocompatible material and/or the geometry of the segments forming the body of the clip.

Another embodiment provides a clip wherein the branches in the first and second segments have tips that grab tissue of the organ when the clip is in the closed or crimping configurations.

Another embodiment provides a clip wherein pressing the proximal portions opens the jaw formed by the crossed branches in the distal portions and wherein releasing the proximal portions closes the jaw formed by the branches thereby allowing grabbing of the tissue by the jaw.

Another embodiment provides a clip further comprising an elastic element disposed between the two segments; wherein the elastic element that enhances the clip grabbing strength by keeping the segments apart.

Another embodiment provides a clip wherein one or both segments have a tip that is straight, pointed, round or flat.

Another embodiment provides a clip wherein one or both segments have tips wherein the tips are covered.

Another embodiment provides a clip wherein the clip is adapted for manipulation through an ancillary.

Another embodiment provides a clip wherein the ancillary allows the clip to adopt one or more configurations as the clip is pushed down by a mobile part of the ancillary.

Another embodiment provides a clip wherein movement of the clip along the length of the ancillary is effected through a button that pushes down the clip.

Another embodiment provides a clip further comprising a space in the body of the clip wherein a grabbing element (for example a hook or atraumatic grasper) can be placed through the space to withdraw the clip from a patient's body cavity.

Another embodiment provides a clip wherein the ancillary is separated from clip by releasing the hook from the clip.

Another embodiment provides a system comprising at least two clips wherein each clip comprises a hole in a segment connecting the first and second segments wherein the two clips can be attached through a flexible string or thread.

Another embodiment provides a system comprising at least three clips 2 wherein each clip comprises a hole in a segment connecting the first and second segments wherein the three clips can be attached through a flexible string or thread to form a Y shape.

Another embodiment provides a system wherein the flexible string is manipulated using a surgical ancillary comprising a stem having a grabbing element (for example a hook) at the end of the stem.

Another embodiment provides a system wherein the string or thread has at least three strands wherein the one of the three strands is a free strand that blocks movement of the string or thread when a mass is suspended through the two clips.

Another embodiment provides a system further comprising a tubular element wherein the thread or string is placed through the tubular element thereby preventing the two clips from collapsing on each other.

Another embodiment provides a system wherein the two clips and string or thread are preassembled in a charging tube having dimensions similar to the dimension of the stem of the ancillary.

Another embodiment provides a system wherein the two clips and string or thread are preassembled in a charging tube having a diameter greater than the diameter of the stem of the ancillary.

Another embodiment provides a system further comprising an element for adjusting the distance between the two clips.

Another embodiment provides a system wherein one or more clips are attached to a net.

Another embodiment provides a system wherein the net allows for holding an organ.

Another embodiment provides a system wherein the net is made of transparent biocompatible material.

Another embodiment provides a system wherein the organ is a liver.

Another embodiment provides a system wherein the net is flat.

Another embodiment provides a system wherein the net has reinforced portions.

Another embodiment provides a system wherein the net has openings where portions of the organ are retained.

Another embodiment provides a system wherein the center of the net forms a cavity for retaining the organ.

Another embodiment provides a system wherein the net has a triangular geometry.

Another embodiment provides a system wherein the system comprises three clips and wherein each of the three clips is attached to one summit of the triangular net.

Another embodiment provides a system wherein the clips are attached to the net through threads with adjustable distances.

Another embodiment provides a system further comprising a mechanism for automatic deployment of the net.

Another embodiment provides a system wherein the net comprises memory alloy wire.

Another embodiment provides a system wherein the memory alloy wire maintains the net in an open position.

Another embodiment provides a system comprising one clip wherein the clip is attached to a band.

Another embodiment provides a system comprising a plurality of clips according to claim 2 wherein each clip is attached to a band and wherein the bands can attach to each other to form a net for moving an organ or tissue.

Another embodiment provides a system wherein the net is assembled within a patient's body cavity during minimal invasive surgery.

Another embodiment provides a system further comprising an element for adjusting the distance between the clip and the band Another embodiment provides a system wherein two or more bands are attached to each other through mechanical means, magnetic means, and/or a glue.

Another embodiment provides a system wherein two or more bands form a shape suitable for moving an organ or tissue.

Another embodiment provides a system wherein at least two bands are attached to form a longer straight band.

Another embodiment provides a system wherein at least two bands are attached to form a T shape.

Another embodiment provides a system wherein at least two bands are attached to form an L shape.

Another embodiment provides a system wherein at least three bands are attached to form a Y shape.

Another embodiment provides a system wherein the bands are attached to each other through hooks.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2: depicts clip configurations according to one embodiment disclosed herein resting configuration (c), open configuration (B), the crimping/grabbing configuration (d), and the sliding configuration (a).

DETAILED DESCRIPTION

Provided herein is a clip for organ retraction or organ exposure during minimal invasive surgery wherein the clip comprises a body made of a biocompatible material wherein the body comprises at least two generally opposing first and second segments that form a jaw; wherein the two segments each comprise distal and proximal ends wherein the proximal ends may be directly connected or connected through one or more segments within the body of the clip and wherein the clip defines at least four configurations a resting configuration, an open configuration, a grabbing configuration, and a sliding configuration.

Figure 1:
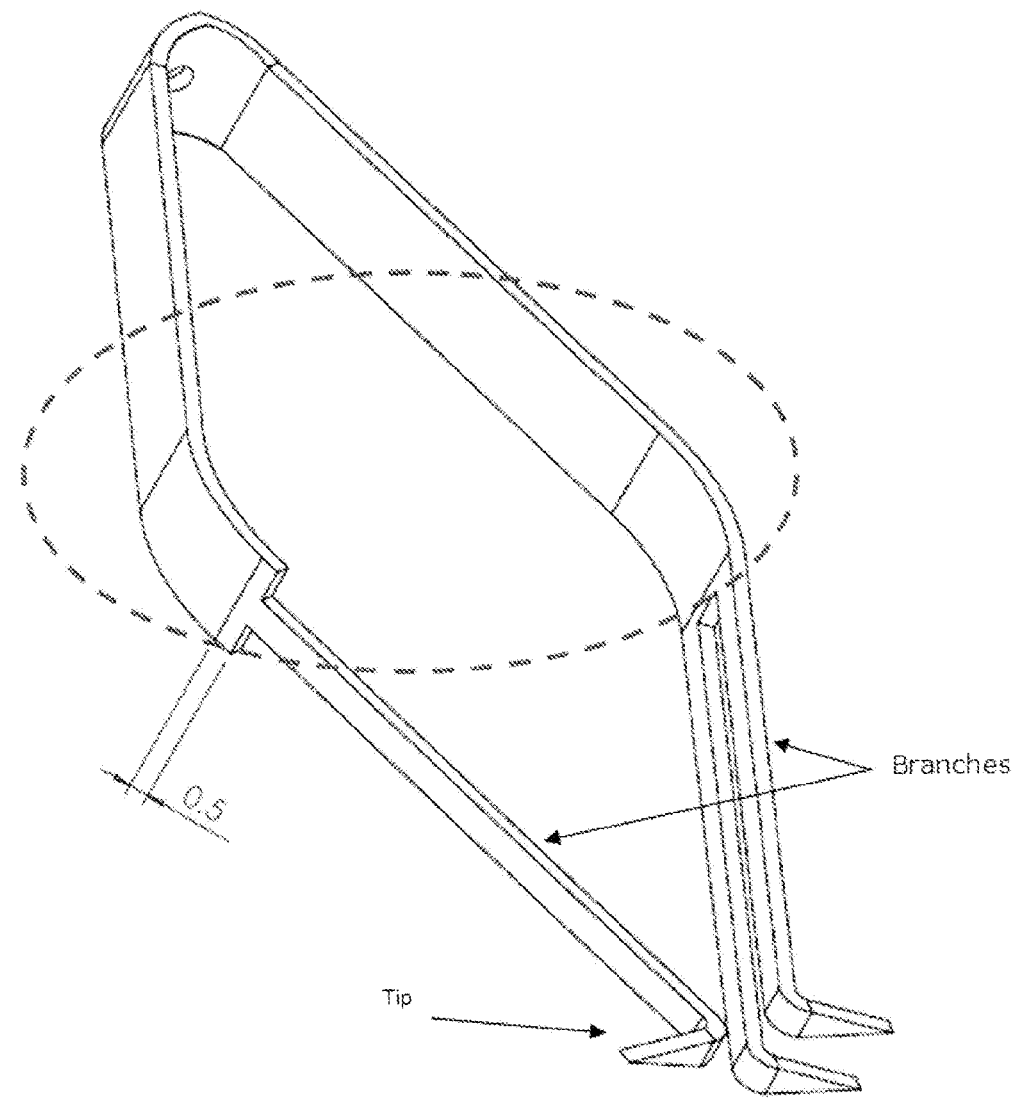
FIG. 1: depicts a clip according to one embodiment as disclosed herein

FIG. 1 shows one illustration of a clip as described herein.

FIGS. 2 A-D illustrate a clip as depicted in Figures one in 4 configurations FIG. 2-A shows the clip in a sliding configuration. FIG. 2-B shows the clip in an open configuration. The open configuration can be obtained by applying pressure on the upper segments of the clip. FIG. 2-C shows a clip in a resting position. The resting position can for example be obtained by releasing pressure on the upper segments of the clip.

FIG. 2-D shows a clip in a grabbing position.

Figure 13:
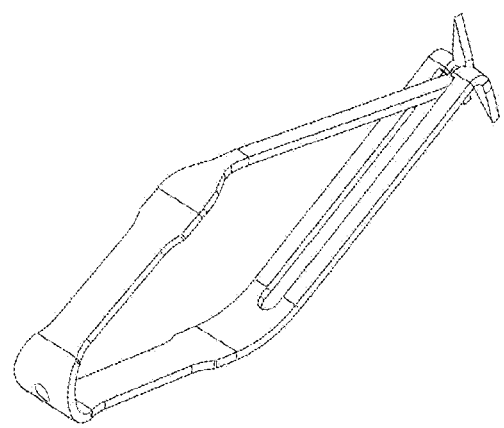
FIG. 13: depicts a clip according to one embodiment as disclosed herein having distal extremities of the two branches that form a U-shape, geometry which retain the single branch inside the U-shape.
Figure 14:
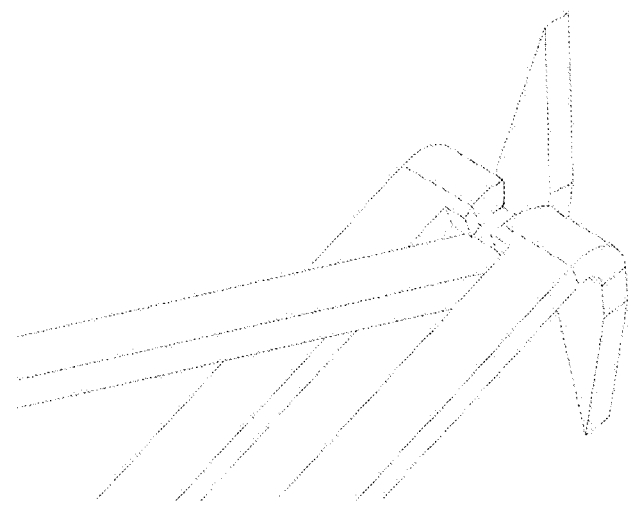
FIG. 14: depicts a partial view of a clip according to one embodiment as disclosed herein having distal extremities of the two branches that form a U-shape, geometry which retain the single branch inside the U-shape.

In one embodiment, in order to enhance the security of the clip, a U-shape geometry is added at the distal extremities of the two branches to retain the single branch inside the U-shape. FIG. 13 depicts a clip according to one embodiment as disclosed herein having distal extremities of the two branches that form a U-shape, geometry which retain the single branch inside the U-shape. FIG. 14 depicts a partial view of a clip according to one embodiment as disclosed herein having distal extremities of the two branches that form a U-shape, geometry which retain the single branch inside the U-shape.

Figure 15:
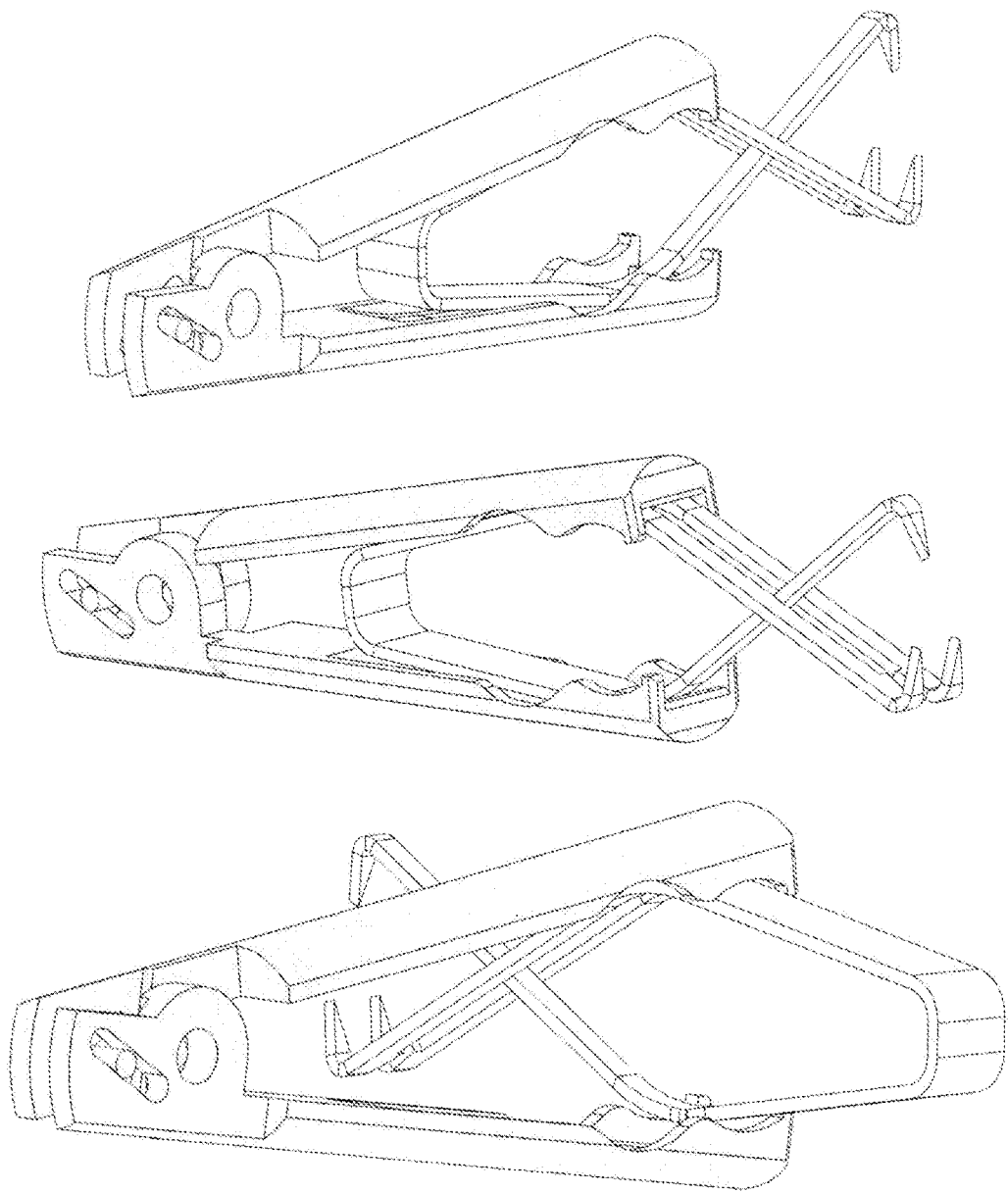
FIGS. 15 (*a, b, c*): depict a clip according to one embodiment within an ancillary or a grasper, wherein the grasper presents specific extremities which correspond to the clip to grab and manipulate it safely longitudinally (a, b) or transversally (c).

In one embodiment an ancillary or a grasper is provided. FIGS. 15 (*a, b, c*) depict a clip according to one embodiment within an ancillary or a grasper, wherein the grasper presents specific extremities which correspond to the clip to grab it safely longitudinally (a, b) or transversally (c).

Figure 4:
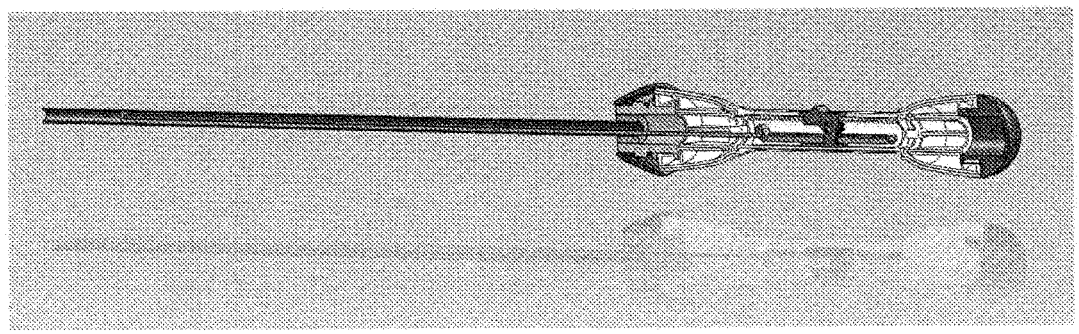
FIG. 4: depicts an ancillary according to one embodiment disclosed herein.
Figure 5:
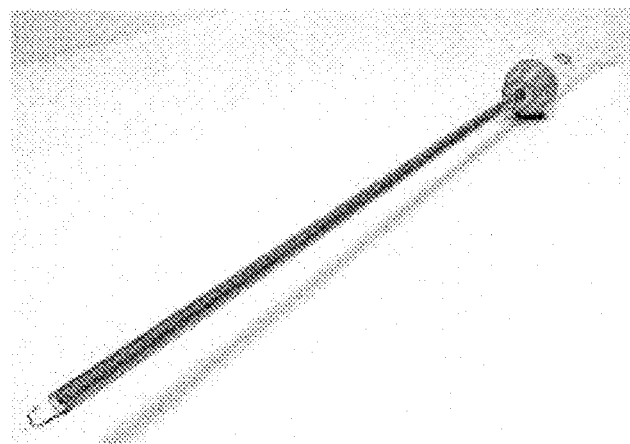
FIG. 5: depicts an ancillary according to one embodiment disclosed herein with a hook illustrating a grabbing element at one end for manipulating a clip as described herein.

Another embodiment provides a clip wherein changing the configuration of the clip is carried out using an ancillary. An ancillary as described herein is illustrated in FIG. 4. An embodiment wherein the ancillary comprising a grabbing element for manipulating the clip is illustrated in FIG. 5. The ancillary can be separated from clip by releasing the grabbing element from the clip.

In one embodiment the ancillary allows in a single movement to change the configuration of the clip from the sliding configuration to the open configuration and then to the grabbing configuration.

In another embodiment the ancillary allows in a single movement to change the configuration of the clip from the sliding configuration to the open configuration and then to the resting.

In another embodiment the ancillary allows in a single movement to change the configuration of the clip to pass from the resting configuration to the open configuration and then to the sliding configuration.

In another embodiment the ancillary allows in a single movement to change the configuration of the clip from the grabbing configuration to the open configuration and then to the sliding configuration Another embodiment provides a clip wherein the distal end of the first segment comprises a single branch and the distal end of the second segment comprises two branches that form a U-shape wherein in a closed configuration of the clip the branch of the first segment fits in the U-shape formed by the two branches of the second segments thereby allowing the two segments to cross. This embodiment is illustrated by the clip of FIG. 1.

Figure 3:
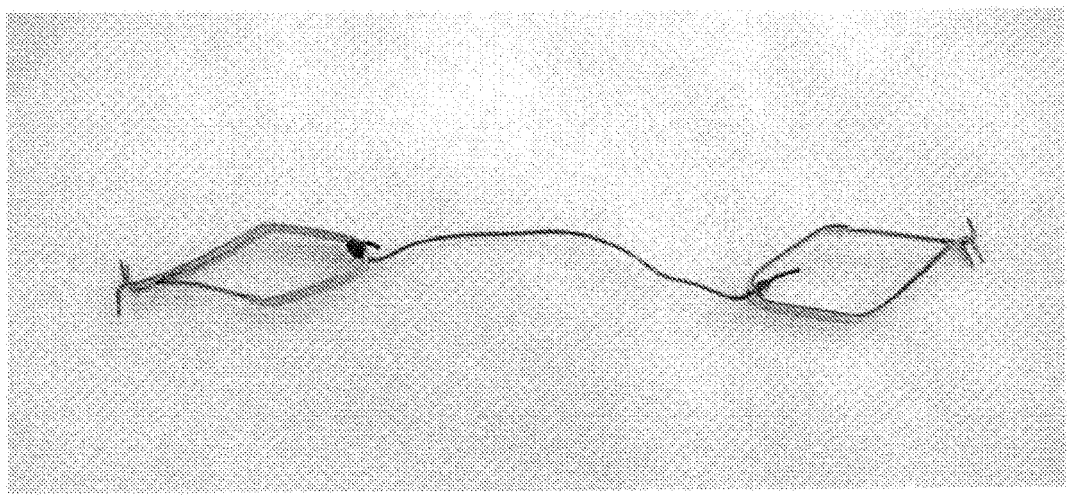
FIG. 3: depicts a system with two clips according to one embodiment disclosed herein attached with a string allowing for adjustment of the distance between the two clips.

Another embodiment provides a system comprising at least two clips wherein each clip comprises a hole in a segment connecting the first and second segments wherein the two clips can be attached through a flexible string or thread. FIG. 3 shows two clips attached through a string.

Another embodiment provides a system wherein the two clips and string or thread are preassembled in a charging tube having dimensions similar to the dimension of the stem of the ancillary. FIG. 7 shows a charger containing two clips for deployment through the ancillary. In one embodiment as described in FIG. 6 shows a charger having a diameter that is slightly greater than the diameter of the ancillary which facilitates sliding the clips through the ancillary.

Figure 6A:
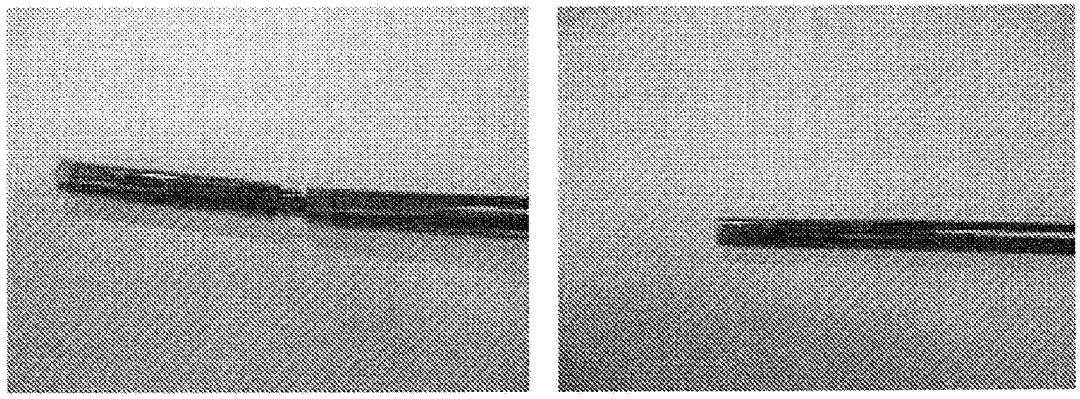
FIG. 6: depicts an embodiment with a clip charging tube and an ancillary tube wherein the charging tube has a diameter slightly greater than the diameter of the ancillary tube.
Figure 6B:
Figure 7:
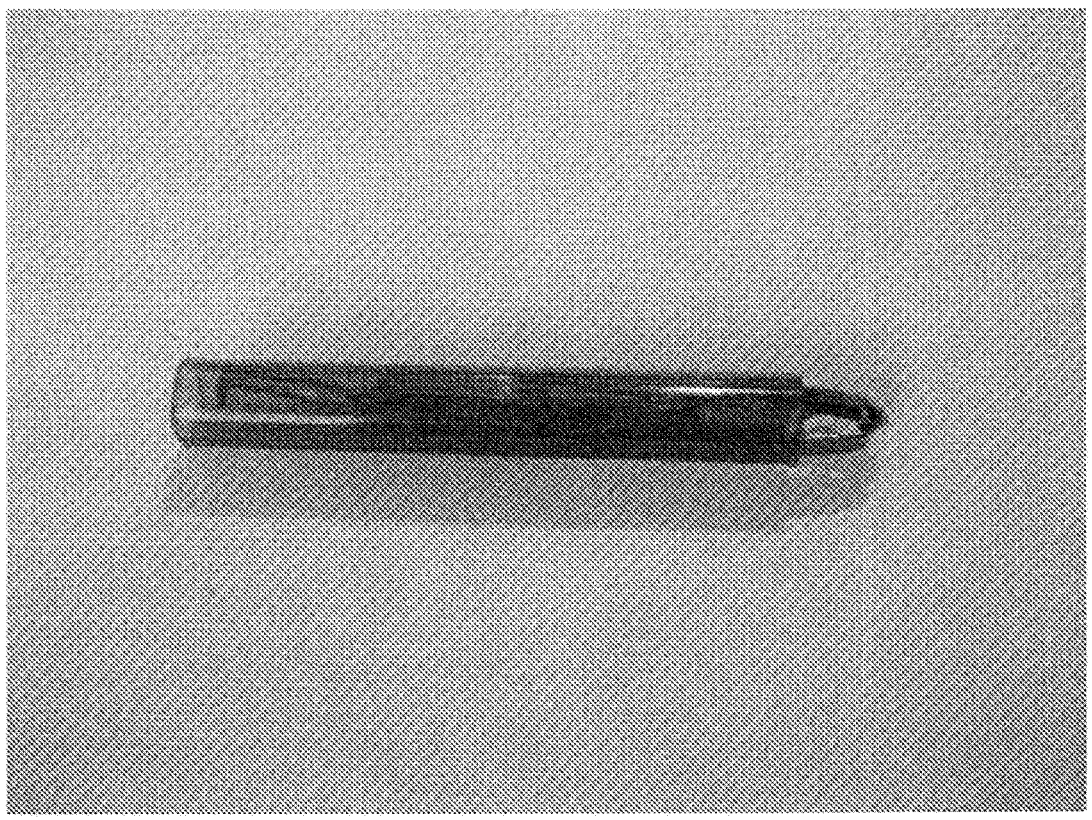
FIG. 7: depicts a charger containing two clips.

Another embodiment provides a system wherein the two clips and string or thread are preassembled in a charging tube having a diameter greater than the diameter of the stem of the ancillary as shown in FIG. 6.

Figure 12:
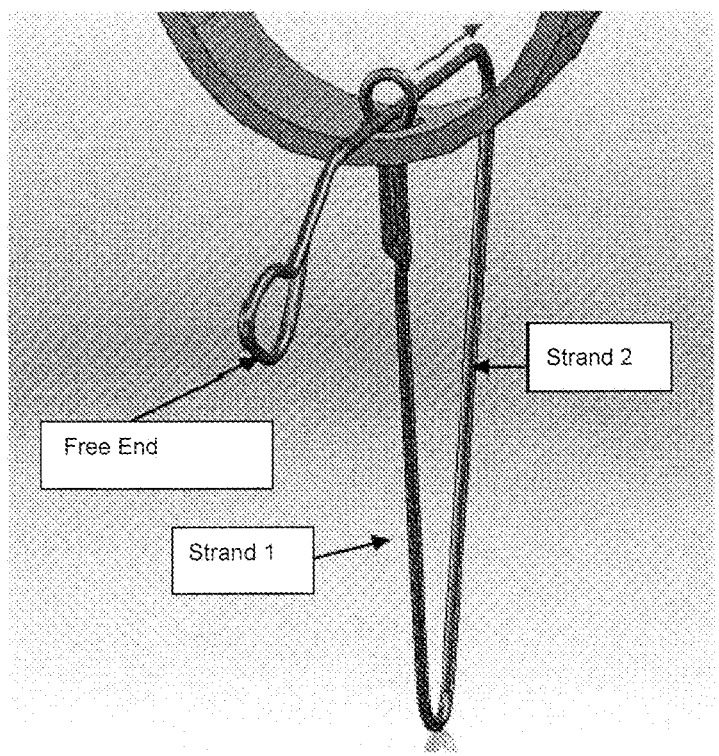
FIG. 12: depicts a system comprising an element for adjusting the distance between two clips.

Another embodiment provides a system further comprising an element for adjusting the distance between the two clips. FIG. 12

Figure 8:
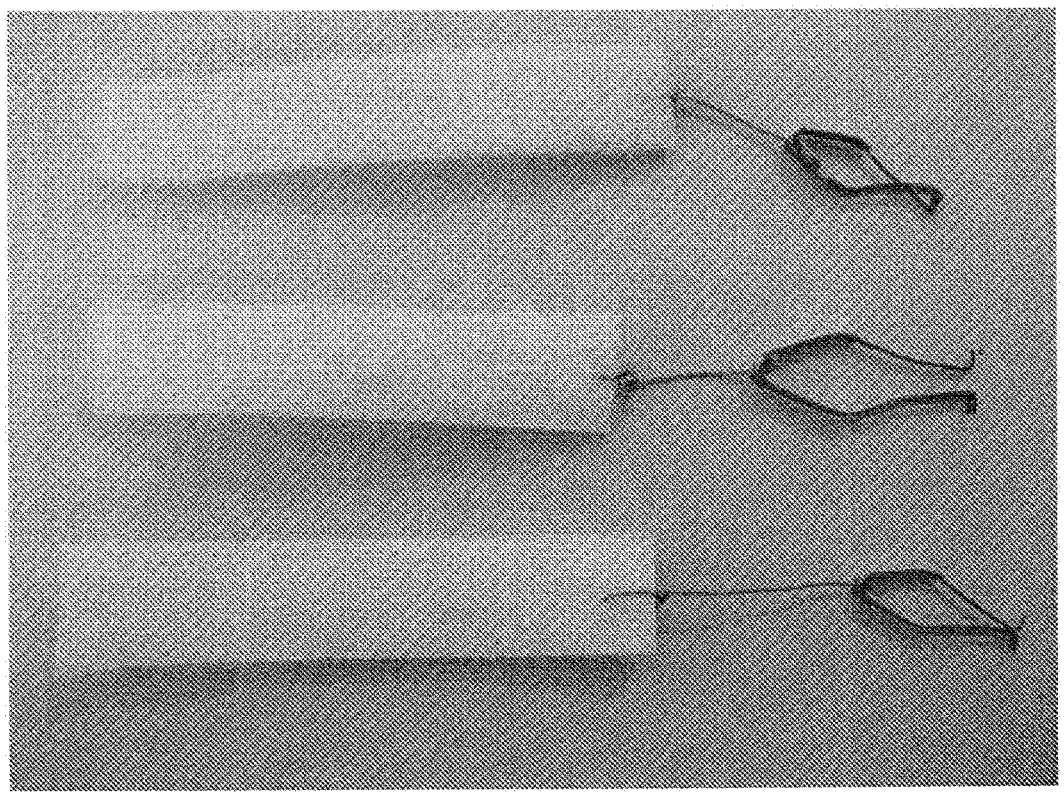
FIG. 8: depicts a system comprising a band attached to a clip according to one embodiment as disclosed herein.

Another embodiment provides a system comprising one clip wherein the clip is attached to a band. One example of a clip attached to a band is shown in FIG. 8.

Figure 16:
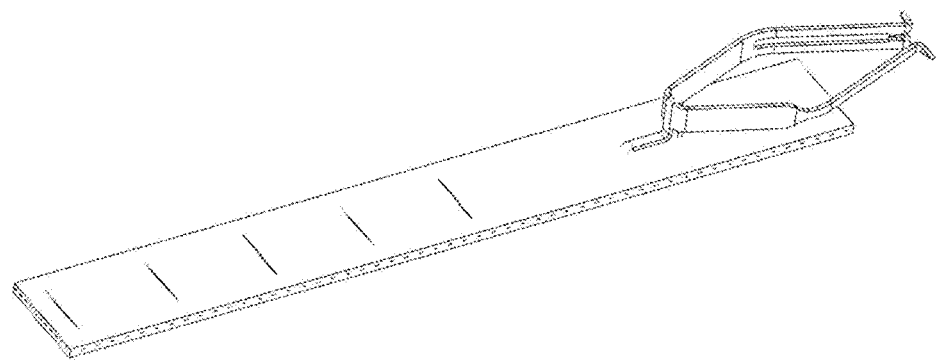
FIG. 16: depicts a system comprising a band attached to a clip according to one embodiment as disclosed herein wherein the system comprising a band made in a material which is elastic in one direction and inelastic on another one; a female portion which is made on the elastic direction wherein small incisions are cut; under traction of this band, the incisions are opening to offer holes enabling the connection with a male band.
Figure 17:
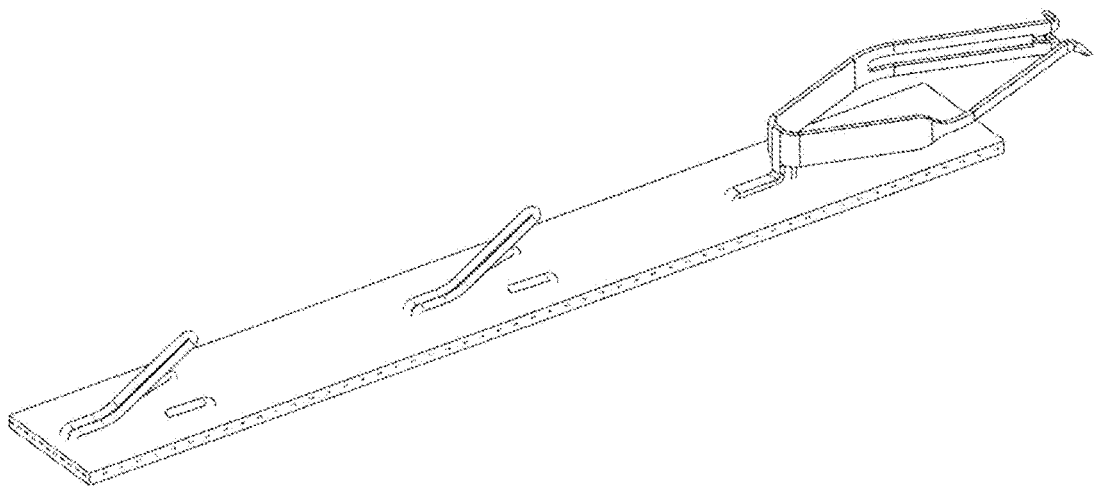
FIG. 17: depicts a system comprising a band attached to a clip according to one embodiment as disclosed herein wherein the system comprising a band made in a material which is elastic in one direction and inelastic on another one; in the inelastic direction hooks are attached which enable the connection with a female bands as depicted in FIG. 16.
Figure 18:
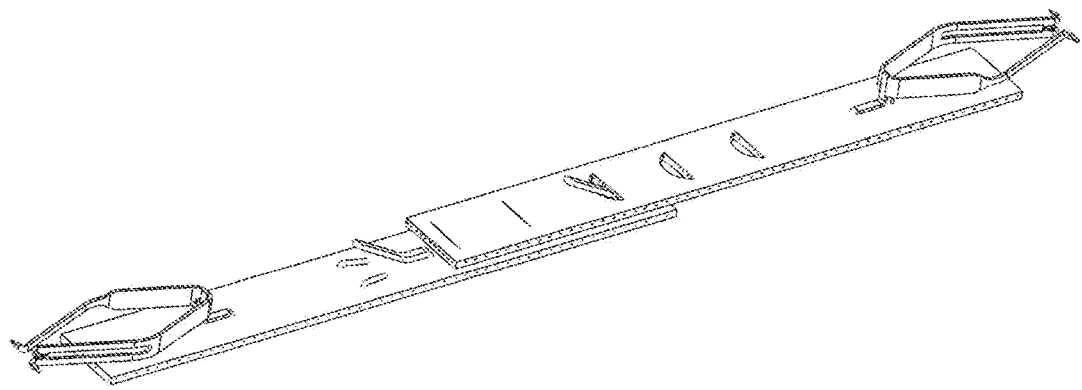
FIG. 18: depicts a system comprising two bands according to FIGS. 16 and 17 wherein the bands are attached by connecting the bands by inserting hooks through the incisions.

Another embodiment provides a system comprising a plurality of clips wherein each clip is attached to a band and wherein the bands can attach to each other to form a net for moving an organ or tissue. One embodiment provides two kinds of bands made in a material which is elastic in one direction and inelastic on another one. For example, a female portion is formed in the elastic direction wherein small incisions are formed. Under traction of this band, the incisions may open to offer holes enabling the connection with a male band comprising a hook. A male band, made o the inelastic direction, on which hooks are connected to facilitate connection to a band having incisions. FIG. 16 depicts a system comprising a band attached to a clip according to one embodiment as disclosed herein wherein the system comprising a band made in a material which is elastic in one direction and inelastic on another one; a female portion which is made on the elastic direction wherein small incisions are cut; under traction of this band, the incisions are opening to offer holes enabling the connection with a male band. FIG. 17 depicts a system comprising a band attached to a clip according to one embodiment as disclosed herein wherein the system comprising a band made in a material which is elastic in one direction and inelastic on another one; in the inelastic direction hooks are attached which enable the connection with a female bands as depicted in FIG. 16. FIG. 18 depicts a system comprising two bands according to FIGS. 16 and 17 wherein the bands are attached by connecting the bands by inserting hooks through the incisions.

Figure 19:
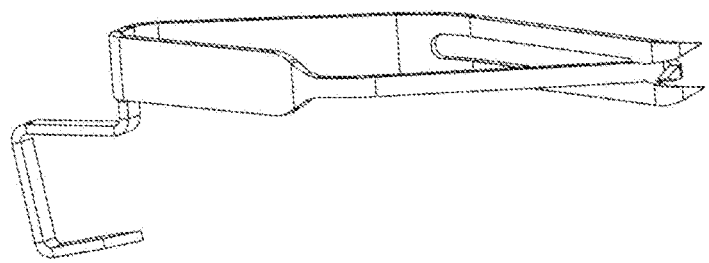
FIG. 19: depicts a clip according to one embodiment as disclosed herein further comprising claws to fix the clip on a substrate.
Figure 20:
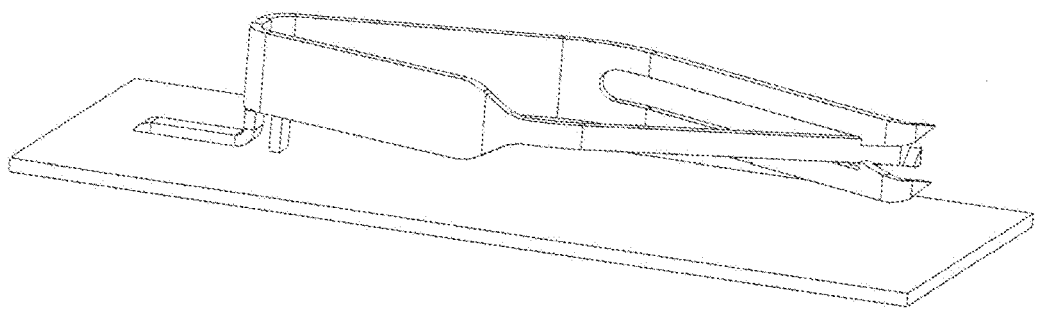
FIG. 20: depicts a clip according to one embodiment as disclosed herein further comprising claws that fix the clip on a substrate.
Figure 21:
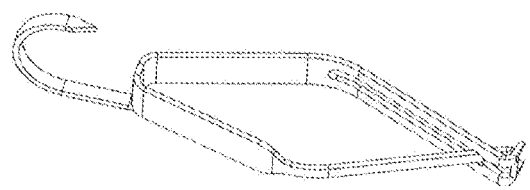
FIG. 21: depicts a clip according to one embodiment as disclosed herein further comprising a claw that can be bent to form a hook enabling the connection of the body of the clip to an organ or a biological tissue.
Figure 22:
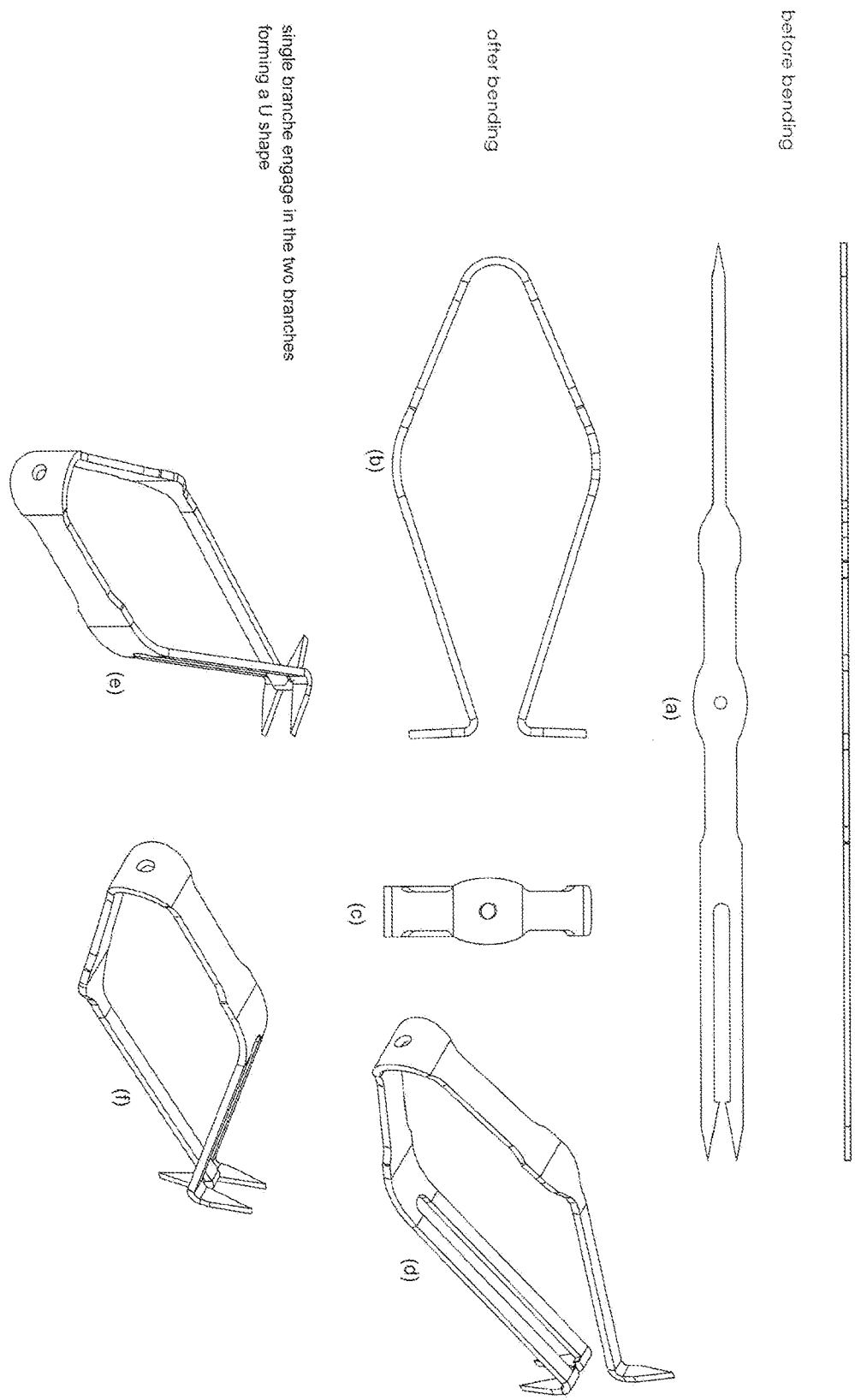
FIGS. 22 (*a, b, c, d, e, f*): depict one embodiment for forming a clip according as disclosed herein.

In one embodiment, claws may be added to the body of the clip to achieve several advantages according to the present disclosure. For example, claws are added to fix the clip on a substrate. The clip presents one or more claws which are bent around some substrate part(s). The clip is therefore linked to the substrate. This embodiment allows the fixation of the substrate on an organ or a biological tissue through the clip. This embodiment also allows preventing biological tissue damage that may be linked to direct contact between the organ and the clip. (Picture 10) FIG. 19 depicts a clip according to one embodiment as disclosed herein further comprising claws to fix the clip on a substrate. FIG. 20: depicts a clip according to one embodiment as disclosed herein further comprising claws that fix the clip on a substrate. FIG. 21 depicts a clip according to one embodiment as disclosed herein further comprising a claw that can be bent to form a hook enabling the connection of the body of the clip to an organ or a biological tissue. The claws can be used to connect different types of accessories to add an additional function to the clip Another embodiment provides a system wherein the net is assembled within a patient's body cavity during minimal invasive surgery.

One embodiment provides a system further comprising an element for adjusting the distance between the clip and the band. FIG. 12

Another embodiment provides a system wherein two or more bands are attached to each other through mechanical means, magnetic means, and/or a glue.

Another embodiment provides a system wherein two or more bands form a shape suitable for moving an organ or tissue.

Figure 9:
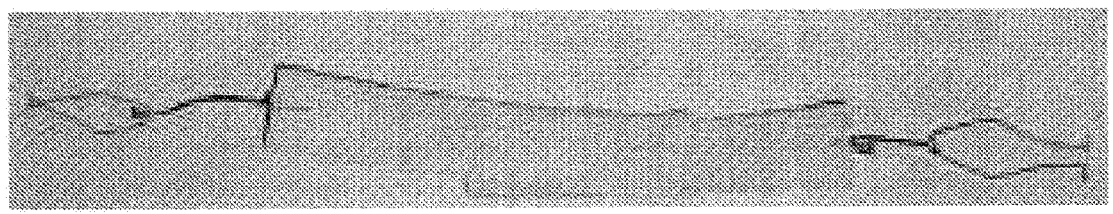
FIG. 9: depicts a system comprising two units each comprising a band and a clip wherein the bands are attached to form a longer band.

Another embodiment provides a system wherein at least two bands are attached to form a longer straight band. FIG. 9 depicts a system comprising two units each comprising a band and a clip wherein the bands are attached to form a longer band.

Figure 10:
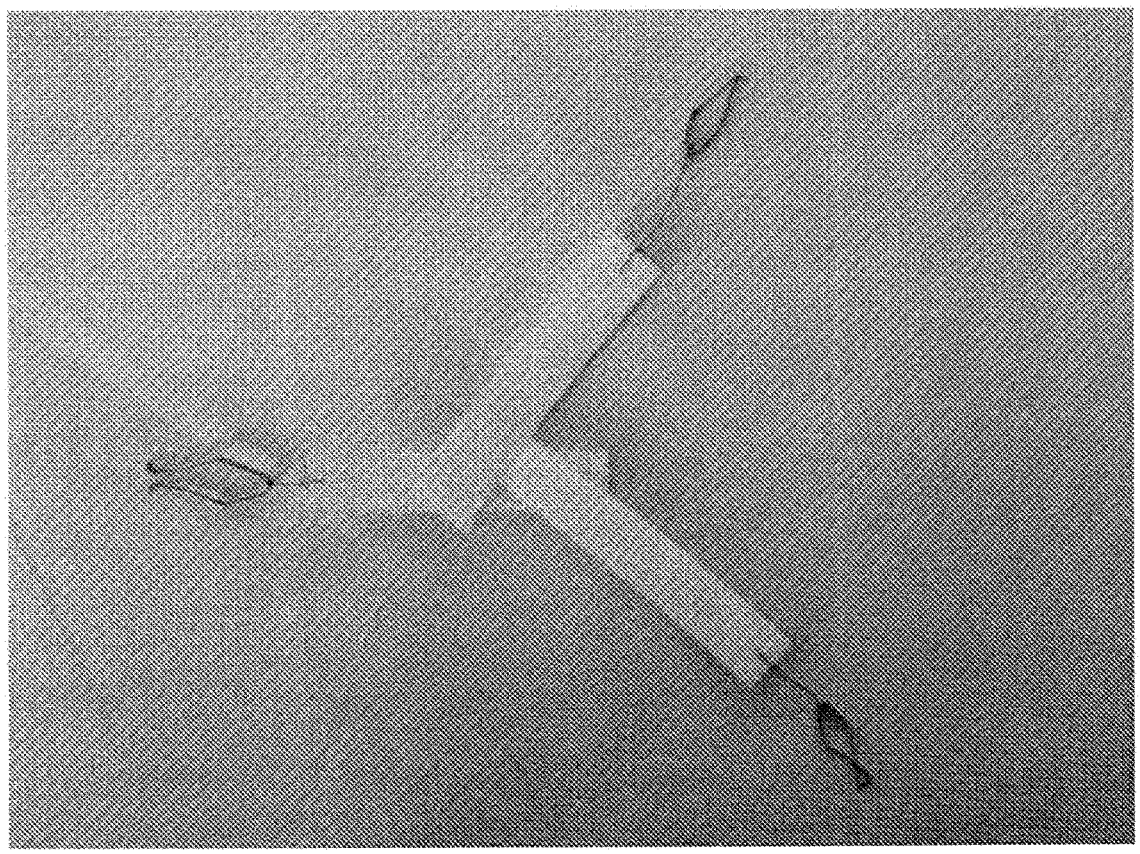
FIG. 10: depicts a system comprising three units each comprising a band and a clip wherein the three bands are attached in the form of a Y.
Figure 11:
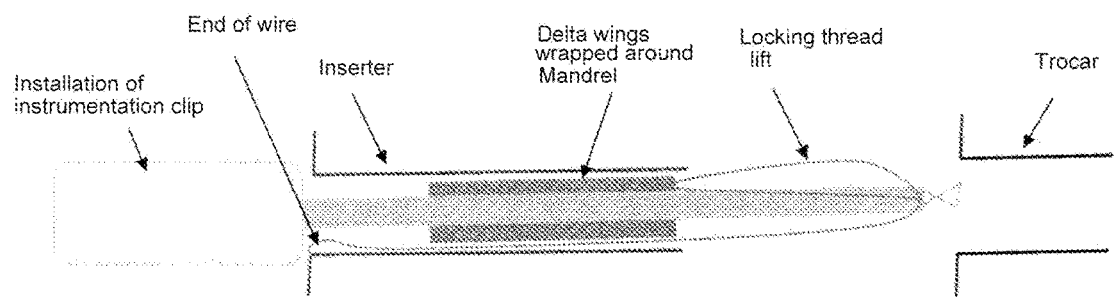
FIG. 11: depicts a system for introducing a clip and a net through a trocar.

FIG. 10 depicts a system comprising three units each comprising a band and a clip wherein the three bands are attached in the form of a Y Another embodiment provides a system wherein the bands are attached to each other through hooks.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A clip for organ retraction or organ exposure during minimal invasive surgery wherein the clip comprises a body made of a biocompatible material wherein the body comprises at least two generally opposing first and second segments that form a jaw; wherein the two segments each comprise distal and proximal ends wherein the proximal ends may be directly connected or connected through one or more segments within the body of the clip and wherein the clip defines at least four configurations; wherein the at least four configurations comprise a resting configuration, an open configuration, a grabbing configuration, and a sliding configuration; wherein the distal end of the first segment comprises a single branch and the distal end of the second segment comprises two branches that form a U-shape; and wherein in the grabbing configuration of the clip the branch of the first segment fits in the U-shape formed by the two branches of the second segment thereby allowing the two segments to cross.

2. The clip of claim 1 wherein the biocompatible material has an elasticity that allows changing the configuration of the clip while the clip is deployed in a cavity of a patient's body.

3. The clip of claim 2 and wherein changing the configuration of the clip is carried out using an ancillary wherein the ancillary allows in a single movement to change the configuration of the clip from the sliding configuration to the open configuration and then to the grabbing configuration.

4. The clip of claim 3 further comprising a space in the body of the clip wherein a hook can be placed through the space to withdraw the clip from a patient's body cavity.

5. The clip of claim 4 wherein the ancillary is separated from clip by releasing a grabbing element from the clip.

6. The clip of claim 2 further comprising an elastic element disposed between the two segments; wherein the elastic element enhances the clip grabbing strength by keeping the segments apart.

7. The clip of claim 1 wherein the clip is adapted for introduction and grabbing of an organ within five minutes or less.

8. The clip of claim 1 wherein the clip is capable of moving an organ or tissue having a weight of up to 2 kg.

9. The clip of claim 1 wherein the clip is capable of moving an organ or tissue having a weight of at least 1.5 kg.

10. The clip of claim 1 wherein the branches in the first and second segments have tips that grab tissue of the organ when the clip is in the closed configuration.

11. The clip of claim 1 wherein the clip is adapted for manipulation through an ancillary and wherein the ancillary allows the clip to adopt one or more configurations as the clip is pushed down by a mobile part of the ancillary.

12. The clip of claim 11 wherein movement of the clip along the length of the ancillary is effected through a button that pushes down the clip.

13. A system comprising at least two clips of claim 1 wherein each clip comprises a hole in a segment connecting the first and second segments wherein the two clips can be attached through a flexible string or thread.

14. A system comprising at least three clips of claim 1 wherein each clip comprises a hole in a segment connecting the first and second segments wherein the three clips can be attached through a flexible string or thread to form a Y shape.

15. A system comprising one or more clips according to claim 1 wherein the one or more clips are attached to a net that allows for holding an organ.

16. The system of claim 15 further comprising a mechanism for automatic deployment of the net.

17. The system of claim 16 wherein the net comprises memory alloy wire.

18. A system comprising one clip of claim 1 wherein the clip is attached to a band.

19. The system of claim 18 further comprising an element for adjusting the distance between the clip and the band.

20. A system comprising a plurality of clips according to claim 1 and a plurality of bands wherein each clip is attached to a band and wherein the bands can attach to each other to form a net for moving an organ or tissue.

21. The system of claim 20 wherein the net is assembled within a patient's body cavity during minimal invasive surgery.

22. The system of claim 20 wherein two or more bands are attached to each other through mechanical means, magnetic means, and/or a glue.

23. The system of claim 20 wherein two or more bands form a shape capable of moving an organ or tissue.

24. The system of claim 20 wherein at least two bands are attached to form a T shape.

25. The system of claim 20 wherein at least two bands are attached to form an L shape.

26. The system of claim 20 wherein at least three bands are attached to form a Y shape.

27. The system of claim 20 wherein the bands are attached to each other through hooks.

28. The clip of claim 1 comprising at the distal ends that form a U-shape a retaining portion to maintain the branch of the first segment inside the U-shape.

29. The clip of claim 1 comprising at the distal ends that form a U-shape a retaining portion to maintain the branch of the first segment inside the U-shape.

30. A system comprising a clip according to claim 1 and a grasper, wherein the grasper presents specific segments which correspond to the clip to grab it safely longitudinally or transversally; wherein the grasper allows to manipulate the clip.

31. The clip of claim 1, further comprising one or more claws to fix the clip on a substrate.

\* \* \* \* \*